US00RE43937E

(19) United States
(12) Reissued Patent
Egalon

(10) Patent Number: US RE43,937 E
(45) Date of Reissued Patent: Jan. 22, 2013

(54) REVERSIBLE, LOW COST, DISTRIBUTED OPTICAL FIBER SENSOR WITH HIGH SPATIAL RESOLUTION

(76) Inventor: Claudio Oliveira Egalon, Los Angeles, CA (US)

(21) Appl. No.: 12/985,521

(22) Filed: Jan. 6, 2011

Related U.S. Patent Documents

Reissue of:
(64) Patent No.: 7,473,906
Issued: Jan. 6, 2009
Appl. No.: 11/410,649
Filed: Apr. 25, 2006

U.S. Applications:
(60) Provisional application No. 60/676,121, filed on Apr. 28, 2005.

(51) Int. Cl.
*G01N 21/64* (2006.01)
(52) U.S. Cl. ..... 250/458.1; 250/459.1; 250/372
(58) Field of Classification Search ..... 250/372, 250/458.1, 459.1, 461.1
See application file for complete search history.

(56) References Cited

U.S. PATENT DOCUMENTS

| | | | | |
|---|---|---|---|---|
| 4,200,110 | A | 4/1980 | Peterson et al. | |
| 4,447,546 | A | 5/1984 | Hirschfeld | |
| 4,582,809 | A | 4/1986 | Block et al. | |
| 4,659,215 | A | 4/1987 | Sumida et al. | |
| 4,820,016 | A | 4/1989 | Cohen et al. | |
| 4,834,496 | A * | 5/1989 | Blyler et al. | 385/12 |
| 4,909,990 | A | 3/1990 | Block et al. | |
| 5,067,815 | A | 11/1991 | Kotrotsios et al. | |
| 5,191,206 | A | 3/1993 | Boiarski et al. | |
| 5,249,251 | A * | 9/1993 | Egalon et al. | 385/123 |
| 5,262,638 | A * | 11/1993 | Egalon et al. | 250/227.14 |
| 5,343,550 | A * | 8/1994 | Egalon et al. | 385/123 |
| 5,577,137 | A | 11/1996 | Groger et al. | |
| 5,701,006 | A | 12/1997 | Schaefer | |

(Continued)

FOREIGN PATENT DOCUMENTS

| | | |
|---|---|---|
| EP | 0 211 587 A | 2/1987 |
| EP | 0211587 A2 | 2/1987 |

(Continued)

OTHER PUBLICATIONS

Pulido, C. et al., "Improved fluorescence signal with tapered polymer optical fibers under side-illumination", Sensors and Actuators B: Chemical, 146, 190, (2010).

(Continued)

*Primary Examiner* — David Porta
*Assistant Examiner* — Marcus Taningco
(74) *Attorney, Agent, or Firm* — Burns & Levinson LLP; Jacob N. Erlich; Marlo Schepper Grolnic

(57) ABSTRACT

A spectroscopic based optical fiber sensor includes a sensitive optical fiber, a probing light source, a power supply, a detector means, a signal processing means, and a display means. The sensitive optical fiber is optically affected by the presence of at least one measurand. The probing light source, adjacent to the sensitive fiber, transversely illuminates the fiber from the outside. The probing light is modified by the sensitive fiber, coupled into the optical fiber core, either as bound modes or leaky modes, as a light signal and guided to a detector means located at the terminus of the optical fiber. The detector means correlates the intensity of the light signal with an electric signal and transmits the electric signal to the signal processing means, wherein the electric signal is correlated to the quantity being measured. The correlated quantity being transmitted and displayed on the display means.

39 Claims, 8 Drawing Sheets

U.S. PATENT DOCUMENTS

| | | | | |
|---|---|---|---|---|
| 5,705,834 | A | 1/1998 | Egalon et al. | |
| 5,747,348 | A | 5/1998 | Jaduszliwer et al. | |
| 6,205,263 | B1 * | 3/2001 | Lieberman et al. | 385/12 |
| 6,328,932 | B1 | 12/2001 | Carter et al. | |
| 6,383,815 | B1 * | 5/2002 | Potyrailo | 436/2 |
| 6,917,735 | B2 | 7/2005 | Murgatroyd et al. | |
| 6,965,709 | B1 | 11/2005 | Weiss | |
| 7,154,081 | B1 | 12/2006 | Friedersdorf et al. | |
| 7,170,590 | B2 | 1/2007 | Kishida | |
| 7,227,123 | B2 | 6/2007 | Kwon, II et al. | |
| 7,244,572 | B1 | 7/2007 | Schwabacher et al. | |
| 7,260,283 | B2 | 8/2007 | Lieberman et al. | |
| 7,268,371 | B2 | 9/2007 | Krames et al. | |
| 7,329,857 | B1 | 2/2008 | Weiss | |
| 7,369,730 | B2 | 5/2008 | Childers | |
| 7,650,051 | B2 | 1/2010 | Lieberman et al. | |
| 2002/0018629 | A1 | 2/2002 | Lieberman et al. | |
| 2003/0142977 | A1 | 7/2003 | Murgatroyd et al. | |
| 2003/0231818 | A1 | 12/2003 | Cantin et al. | |
| 2004/0223151 | A1 | 11/2004 | Petros et al. | |
| 2005/0053344 | A1 | 3/2005 | Lieberman et al. | |
| 2005/0074208 | A1 | 4/2005 | Badcock et al. | |
| 2006/0147149 | A1 | 7/2006 | Lieberman et al. | |
| 2007/0286547 | A1 | 12/2007 | Lieberman et al. | |

FOREIGN PATENT DOCUMENTS

| | | | |
|---|---|---|---|
| EP | 0 371 675 | A | 6/1990 |
| EP | 1 079 252 | A2 | 2/2001 |
| GB | 2 213 954 | A | 8/1989 |
| JP | 10 013 345 | A | 1/1998 |
| WO | WO0171316 | | 9/2001 |
| WO | WO 03 044 567 | A2 | 5/2003 |

OTHER PUBLICATIONS

U.S. Appl. No. 09/535,300, filed May 16, 2001, Schwabacher et al.

Lieberman et al., "A distributed fiber optic sensor based on cladding fluorescence", J. Lightwave Tech., vol. 8, No. 2, Feb. 1990, pp. 212-220.

Prince et al., "A Readout Scheme Providing High Spatial Resolution for Distributed Fluorescent Sensors on Optical Fibers", Analytical Chemistry, vol. 73, No. 5, Mar. 1, 2001.

Mendoza et al., "Distributed fiber optic chemical sensors for detection of corrosion in pipelines and structural components", SPIE Proceedings, vol. 3398, pp. 136, Mar. 1998.

Albin, Sacharia; Bryant, Alvin L.; Egalon, C. O. and Rogowski, R. S., "Injection efficiency from a side excited thin film fluorescent cladding of a circular waveguide", Optical Engineering, vol. 33, No. 4, pp. 1172-1175, Apr. 1994.

A. Bryant; S. Albin; C.O. Egalon and R.S. Rogowski "Changes in the amount of core light injection for a fluorescent clad optical fiber due to variations in the fiber refractive index and core readius: experimental results", J. Opt. Soc. of America B, vol. 12, No. 5, pp. 904-906, May 1995.

Fitzpatrick et al., "A novel multi-point ultraviolet optical fibre sensor based on cladding luminescence", Meas. Sci. Technol. vol. 14, pp. 1477-1483, 2003.

Egalon, Claudio O., "Modelling an Optical Fiber Bragg Grating", Ph.D. Dissertation, Old Dominion University, Dec. 1996.

Dietrich Marcuse, "Launching light into fiber core from sources located on the cladding", Journal of Lightwave Technology, Aug. 1988, p. 1273, vol. 6, No. 8.

* cited by examiner

REVERSIBLE, LOW COST, DISTRIBUTED OPTICAL FIBER SENSOR WITH HIGH SPATIAL RESOLUTION

Matter enclosed in heavy brackets [ ] appears in the original patent but forms no part of this reissue specification; matter printed in italics indicates the additions made by reissue.

CROSS REFERENCE TO RELATED APPLICATIONS

The present application claims priority from U.S. Provisional Application Ser. No. 60/676,121, filed Apr. 28, 2005.

BACKGROUND

1. Field of Invention

This invention relates generally, to spectroscopic based optical fiber sensors. Particularly, this invention relates to absorption, fluorescent, phosphorescent and chemiluminescent based sensors.

2. Description of Prior Art

Spectroscopic based optical fiber sensors are used throughout numerous industries for the detection of temperature and various chemical species comprising a liquid or gas. These sensors have been developed using, primarily, two separate approaches: the optrode (or optode) and the distributed sensing approach.

Optrodes are the simplest type of optical fiber sensors. Peterson et al, U.S. Pat. No. 4,200,110, discloses an indicator at the distal end of the fiber that is excited by a light source located in the proximal end. The excitation light travels through the fiber and interacts with the indicator producing a spectral signal (fluorescence, phosphorescence, chemiluminescence and/or absorption). The signal travels back to the proximal end, is collected by a detector and is correlated with the parameter that is being measured. In this case, the fiber, having no sensitive regions along its length to produce a change in the signal, serves only as a conduit of the light, which propagates undisturbed from the proximal fiber end to the indicator and back. Each point along the fiber sensor requires a separate fiber optically communicating between the light source and the indicator, potentially creating a complex system of several of fibers.

In the distributed sensing approach, the entire fiber or sections of the fiber, act as a sensor. In one case, the fiber is manufactured with a single cladding sensitive to the parameter being measured. In another case, several cladding sections are removed exposing the fiber core. Next, the bare core regions are coated with a reactive agent, often having an index of refraction similar to that of the cladding. In either approach, these reactant regions can be probed by an excitation light. Not only does the fiber act as a conduit for the signal, the fiber itself is sensitive, resulting in a multipoint, quasi distributed, sensing device. Whereas, the optrode approach requires several strands of optical fibers to make multiple spatial measurements, the distributed sensing approach usually requires just a single optical fiber strand. Therefore, the advantage of distributed sensing is that it can make multiple spatial measurements with a single device.

Within the distributed sensing approach, there are two primary methods for probing to the sensitive regions of the fiber, axial excitation and transverse excitation, transverse excitation being judged to be a superior technique by the present invention.

Axial excitation is commonly used as a means for probing the sensitive cladding. In axial excitation, light that is injected from one end of the fiber, along the axis, interacts with the surrounding cladding via its evanescent wave tail. The cladding absorbs the excitation light in the evanescent region producing either an absorption or luminescent signal that can be detected at the end of the fiber.

The axial excitation technique, however, has various inherent drawbacks. The interaction between the evanescent tails of the excitation light with the sensitive cladding is very small requiring a high power source, an expensive detection scheme and/or a very long optical fiber. Additionally, depending on the arrangement, the collinear alignment of the light source (such as a laser) with the axis of the optical fiber can be challenging, possibly requiring careful handling and calibration.

Schwabacher, international publication number WO 01/71316 ('316), demonstrates a linear array of chemosensors arranged along an optical fiber, each reactant region in the array being sensitive to a chemical species. Each successive reactant region is separated by a substantially inert region, such as cladding. This substantially inert region must have a minimum length, the preferable length being stated as 250 cm. Publication '316 demonstrates both the axial and transverse methods of excitation, axial being the preferred mode.

In the preferred embodiment, '316 employs a narrow axial laser pulse to introduce an excitation light to the optical fiber. Each reactant region is separated by a minimum distance along the fiber, the region between the reactive regions being substantially inert. This relative long inert section is required by the technology utilized by '316, to prevent overlap of fluorescent traces from successive reactant regions. An excitation light from a source (such as a laser, diode laser, gas laser, dye laser, solid state laser, LED, etc) is introduced axially to an optical fiber, the light then being delivered to the reactant regions.

In order to determine which reactant region, among several or even hundreds, is producing a signal, the time delay between the excitation pulse and return signal must be precisely known and correlated with the distance each particular reactant region is from the source, measuring time, distance, and wavelength by use of precise instruments such as the oscilloscope and photomultiplier tube. This arrangement requires an extremely long length of fiber in order to measure hundreds of species, increasing the overall size and complexity of the analyzing device. Furthermore, the precision instruments can increase the overall cost of the instrument significantly.

The excitation light can also be introduced to the reactant regions on the sensing fiber by an excitation fiber or fibers. This also requires the axial introduction of light to the excitation fiber. One excitation fiber per reactant region is required in one embodiment, each fiber introducing the excitation light transversely to the reactant region of the sensing fiber.

Another embodiment requires the use of beam splitters to deliver the excitation light transversely to the reactant regions. The beam splitting technique make use of expensive high power lasers wherein the intensities decay as more beam splitters divert the excitation light to the sensitive coating.

In another scheme, the excitation fiber is prepared by removing its cladding from small sections along its length, these sections then being installed adjacent to the reactant regions on a nearby sensing fiber, allowing its evanescent field to transversely excite the sensing fiber. A disadvantage is that the evanescent field of the excitation fiber is very weak delivering very little power to the sensing fiber. Additionally, other methods of axial and transverse excitation are revealed; however, these methods were, on average, not cost effective.

Although it is acknowledged that these embodiments of '316 are operational, they are limited by complexity, manufacturing expense, and robustness of design. In order to manufacture alternating sections of reactant and inert regions, cladding must be removed only in the reactant regions, leaving it intact in the inert regions. This alternating removal of cladding increases the expense and complexity of mass production, limiting automation options in manufacture.

Additionally, other techniques utilized in industry require the use of expensive instrumentation such as an optical time domain reflectometer (OTDR). Costing on the order of U.S. $20,000 or more, the OTDR adds considerable expense to any system that uses the axial excitation technique. Also, the wavelengths availability of the OTDR systems are limited, restricting the choices of reagents that can be used with the sensor. A further disadvantage of present systems is interference of the signal detected by the OTDR caused by inadvertent bends and physical irregularities in the waveguide material, varying the fiber's refractive index. Furthermore, present techniques lack refinement of spatial resolution, on the order of approximately 10 cm. A more refined spatial resolution is needed.

Again, it is acknowledged by this inventor that transverse excitation of the sensitive region is a superior technique, producing a substantial quantity of fluorescent signal. However, past inventors failed to identify that side excitation, when properly done, can probe very small sections of a sensitive fiber leading to a sensor with a very high spatial resolution. High spatial resolution, less than 5 mm, is desired in applications wherein there is a strong variation of the temperature and/or concentration of a chemical species along the length of the optical fiber. The monitoring of chloride ions in concrete structures, serves as an example where the sensing can be made at discrete narrow locations along the fiber. Previous endeavors also failed to provide a simpler excitation technique that leads to a low cost and rugged sensor.

What is needed is an inexpensive probing light source that can additionally provide a high spatial resolution to the fiber sensor, on the order of 5 mm or less, enabling the pinpointing of the exact location of detection. What is needed, additionally, is a cost effective optical fiber sensor system that uses inexpensive, off the shelf, commercially available devices that can be fabricated by automated means. What is also needed is a flexible device that can be used throughout the infrared, visible, and ultraviolet regions of the electromagnetic spectrum. Additionally, what is needed is a rugged sensing device that can be easily aligned and is not affected by outside interference such as bending and ambient light. In addition, a generic design that can be adapted to monitor different chemical species is needed. What is also needed is an intense, and yet, cost effective probing light source for a fluorescent based and absorption based fiber that can produce a strong signal that can be easily detected. And what is finally needed, is a modular sensing system design that can be easily updated with the evolving technology.

SUMMARY OF THE INVENTION

In accordance with the present invention a reversible, rugged, inexpensive, distributed optical fiber sensor with high spatial resolution is presented. The present invention can be used throughout the infrared, visible, and ultraviolet regions of the electromagnetic spectrum. The light source of the present invention provides an intense, and yet, cost effective means for probing the sensitive region of the fiber and produces a strong signal that can be easily detected.

The present invention can be doped with various sensitive coatings, each being sensitive to a particular chemical species. And, the present invention can be continually updated with new doping means and chemicals, new probing light sources, new sensors, and new computing codes.

The preferred embodiment of the present invention is generally comprised of a sensitive optical fiber, a probing or excitation light source, a power supply, a detector means, a signal processing means, and a display means. The probing or excitation light source is in close proximity and in direct optical communication with the sensitive region of the optical fiber. The optical fiber is sensitive to temperature and/or at least one chemical species, and is optically affected, in a monotonic relationship, by these measurands. The sensitive optical fiber transversely receives a probing light from the light source, the probing light interacting with the sensitive region of the optical fiber. The sensitive region of the fiber, upon being probed, modifies the probing light generating a light signal that is affected by the temperature and/or the presence of a chemical species. The light signal is coupled into the optical fiber core as a light signal and guided to a detector means, which is in axial optical communication with the terminal end of the fiber. The detector means correlates the intensity of the light signal with an electric signal. The electronic signal is transmitted to the signal processing means, wherein the electronic signal is correlated with the measurand (temperature, concentration of chemical species, etc.) that is being measured. The correlated quantity is transmitted and displayed on the display means.

Either a portion or the entire area surrounding the core of the optical fiber is sensitive to the chemical species being measured. A sensitive dope is either incorporated throughout a permeable cladding or applied directly to the bare core. The resulting sensitive fiber is preferably reversible, consistently returning to a reference intensity signal.

In a preferred configuration, the probing light source is a UV LED, positioned adjacent to the optical fiber, and illuminating its sensitive region. The UV LED was chosen for several reasons. Primarily, the UV LED is an inexpensive and readily available source of excitation light, decreasing manufacturing expense. Secondly, recent LED technology has improved the intensity and decreased the size of the UV LED, allowing for a narrow, intense interrogating light beam. Additionally, the close proximity of the UV LED to the optical fiber allows for an increased intensity of the light signal, enabling the use of an inexpensive detector means, such as a silicon photo detector. Finally, the small LED size enables illumination of small regions of the cladding at multiple positions along the fiber length resulting in multiple independent sensing points with high spatial resolution. The technique also allows for the exact locating of the point of detection in a substance, showing a variation in the temperature and concentration of a chemical species along the length of the fiber.

An additional embodiment can include a reflector at the terminus of the optical fiber opposite of the detector means, increasing the light signal through redirecting backward propagating modes towards the detector means.

Yet another embodiment includes the use of a sensitive optical fiber with a tapered core, generally diverging towards the detector as the light signal propagates from the sensitive region of the optical fiber to the detector. This core configuration has the advantage of coupling more light into the fiber core than the other configurations increasing the signal of the device. With a tapered optical fiber, light rays that otherwise would radiate away from the fiber core are coupled as low loss bound modes and propagate for much longer lengths. This fiber can be manufactured using a drawing tower with a tapered glass preform. Alternatively, this fiber can also be manufactured manually by skilled in the shaping of glass.

In yet another embodiment, a plurality of light sources are positioned in a linear array along the length of the sensitive optical fiber, each light source consecutively, simultaneously, or independently emits a probing light transverse to the optical fiber core. The length of the array corresponds substantially to the length of the sensitive region of the optical fiber. This arrangement can be used to increase the overall light intensity of the coupled light signal.

An alternate embodiment uses an excitation optical fiber to transversely excite the sensitive optical fiber. In this case, the excitation fiber serves as a light guide for the excitation light and is deployed parallel to the sensitive optical fiber. The excitation fiber is manufactured with a reflecting distal end face at an angle of approximately 45 degrees, although other angles may also work, which redirects the probing light towards the sensitive optical fiber. The probing light is generated by a light source at the proximal end of the fiber, and introduced axially. The position of the distal end of the excitation fiber can be changed to probe different sections of the sensing fiber; or multiple excitation fibers can be used, each probing a specific area of the sensitive optical fiber.

Yet another alternate embodiment uses an excitation optical fiber having several long period Bragg gratings. This excitation fiber is also deployed along the sensitive optical fiber and illuminates, or probe, several of its sections through the long period gratings. Each grating is designed to couple light from a bound mode core of the sensitive optical fiber into radiation modes at specific wavelengths, $\lambda_i$, within the absorption spectrum of the sensitive dye. In this case, the light from a broadband light source passes through a monochromator that scans the wavelengths within the absorption spectrum of the dye. When the monochromator is tuned to a wavelength $\lambda_1$ only the grating tuned to this wavelength couples the light towards the sensitive optical fiber and the illuminated section corresponds to the position of this specific Bragg grating. The procedure can be repeated for other wavelengths.

An additional embodiment uses an active core optical fiber doped with a substance that amplifies the signal from the sensitive region. This embodiment works in a way similar to that of an optical fiber amplifier. Accordingly, the signal from the sensitive coating is coupled into the fiber core. The active core is then excited by the light modified by the sensitive coating amplifying the original signal. This amplified signal is then guided to the detector. This embodiment is preferred whenever long lengths of fiber are used.

The present invention, and its alternate embodiments, can be used either with a fluorescent reagent or with an absorption based reagent. It can also be used to determine both a given chemical species as well as temperature by choosing an appropriate reagent. Reagents sensitive to a given chemical species are commercially available as are temperature sensitive materials. Fluorescent reagents, such as lucigenin, can be used to detect chloride ions. Similarly, commercially available thermo-phosphors materials have their fluorescence affected by temperature changes. For instance, Europium-doped lanthanum oxysulfide, europium-doped gadolinium oxysulfide and europium-doped yttrium oxysulfide (see Wickersheim, U.S. Pat. No. 4,560,286) are thermophosphors that can be used with this invention to detect temperature.

The present invention is designed to substantially improve optical fiber sensing systems by, primarily, transversely positioning the light source, such as a UV LED or a white light LED, directly adjacent to the sensitive region of the sensitive optical fiber. This arrangement increases the intensity of the coupled light signal, decreases complexity and manufacturing costs, and, when using LEDs with small sizes, allows for the exact locating of the point of detection in a substance with a high spatial resolution.

DESCRIPTION OF THE PREFERRED EMBODIMENTS

The following detailed description is of the best presently contemplated mode of carrying out the invention. This description is not to be taken in a limiting sense, but is made merely for the purpose of illustrating general principles of embodiments of the invention. The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Figure 1:
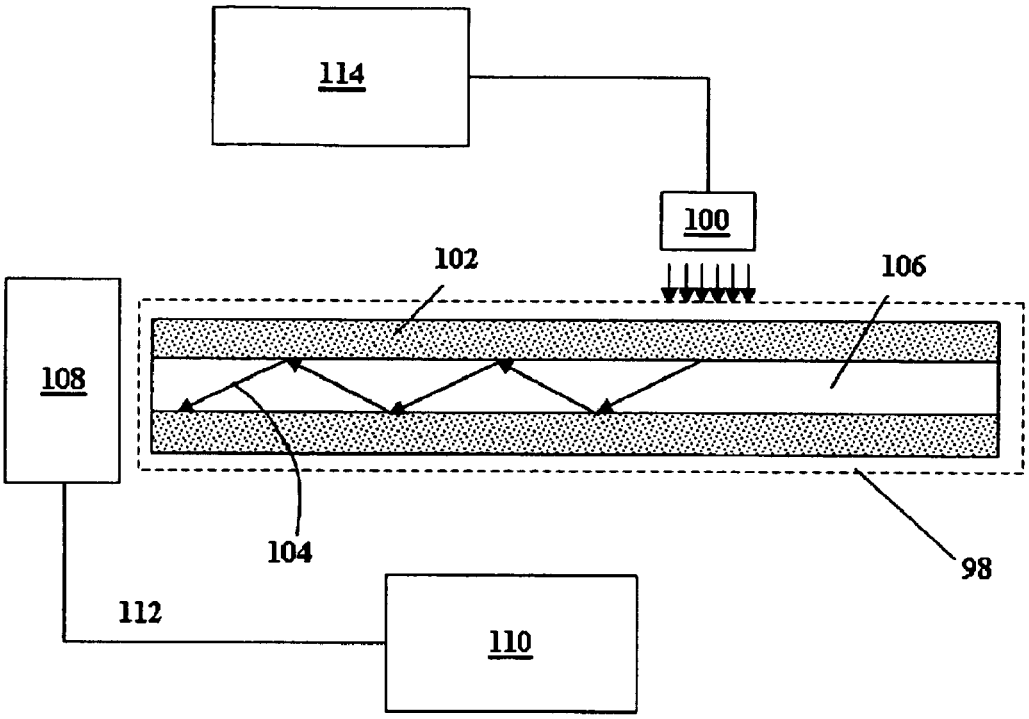
FIG. 1 is a block diagram showing the operation of the present invention using a fluorescent indicator.

A block diagram of the sensor 98 is shown in FIG. 1. Accordingly, an excitation (probing) UV light source, such as a UV Light Emitting Diode (UV LED) 100, transversely illuminates a section of the sensitive cladding 102, made of a fluorescent material, generating fluorescence 104, the illuminating light shown as arrows. The UV LED 100 is attached to a power supply 114 that provides the current to the UV LED 100, the UV LED 100 being positioned in close proximity and in optical communication to the sensitive cladding 102.

A fraction of the fluorescence 104 is coupled into the fiber core 106 and guided to a detector 108, such as a silicon photo-detector, which correlates the light intensity of the fluorescence 104 to an output electrical signal. This electrical signal is transmitted to a signal processing means 110, such as a multimeter, via a cable 112. At the signal processing means 110, the signal is amplified and its optical intensity is displayed. The intensity read by the signal processing means 110 is then correlated with the concentration of the chemical species surrounding the sensor 98.

Figure 1A:
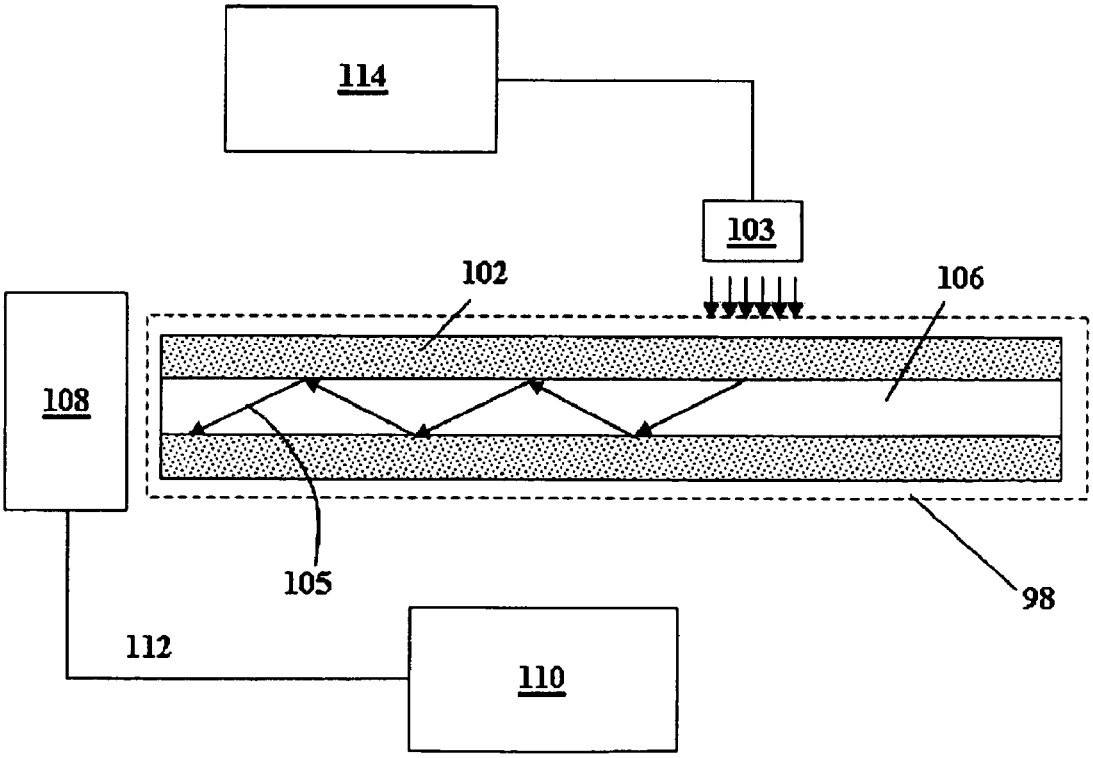
FIG. 1A is a block diagram showing the operation of the present invention using a absorption based indicator.

A similar approach can also be used for an absorption based sensitive optical fiber as shown in FIG. 1A. Accordingly, a probing light source, such as a white light Light Emitting Diode (White LED) 103, transversely illuminates a section of the sensitive cladding 102, made of an absorption based dye, the illuminating light shown as arrows. The probing light source 103 is attached to a power supply 114 that provides the current to the probing light source 103 which is positioned in close proximity and in optical communication to the sensitive cladding 102.

The original probing light is filtered out by the sensitive absorption based cladding 102 and a fraction of the filtered light is coupled into the fiber core 106 as low loss leaky modes 105. The low loss leaky modes 105 are then guided to a detector 108, such as a silicon photo-detector, which correlates the light intensity of the absorbed light to an output electrical signal. This electrical signal is transmitted to a signal processing means 110, such as a multimeter, via a cable 112. At the signal processing means 110, the signal is amplified and its optical intensity is displayed. The intensity read by the signal processing means 110 is then correlated with the concentration of the chemical species surrounding the sensor 98.

As an example, commercially available reactive dyes, such as Lucigenin, have their fluorescence output attenuated by chloride ions and can be used as an indicator for this ion. Accordingly, high signal output corresponds to a low concentration of chloride ions and vice versa. Similarly, the commercially available absorption based dye, Reichardt's dye, can be used to determine relative humidity. Accordingly, a high signal output corresponds to high relative humidity levels.

By controlling the position of the illumination or the probing light source, it is possible to probe different sections of the fiber 98 creating a multiple point sensor. Either the UV LED 100 can be transported to various sections of the fiber 98 having different reactant agents, or each reactant section can individually be illuminated by a corresponding UV LED 100. With a diameter as small as 5 mm, recently introduced, commercially available UV LEDs 100 can help achieve a spatial resolution equal to the illuminated section of the sensitive region of the fiber 98 whose section length is comparable to the diameter of the UV LED 100.

Figure 2:
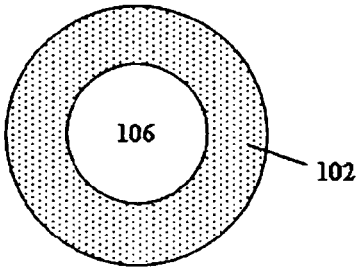
FIG. 2 is a cross sectional view of the sensing fiber of the present invention.

Looking more particularly at FIG. 2, one can see the cross section of the optical fiber 98 of the present invention, with a glass or plastic core 106 surrounded by a fluorescent cladding 102, sensitive to chloride ions in this instance. A sensitive dope is either permeated throughout the inert cladding 102 or applied directly to the bare core 106.

The heart of the sensor 98 is an optical fiber core 106 coated with a polymeric material doped with a fluorescent dye sensitive to the measurand that is intended to be measured. The polymeric material and the fluorescent dye, when coated over the fiber core 106, form the fluorescent cladding 102.

Figure 2A:
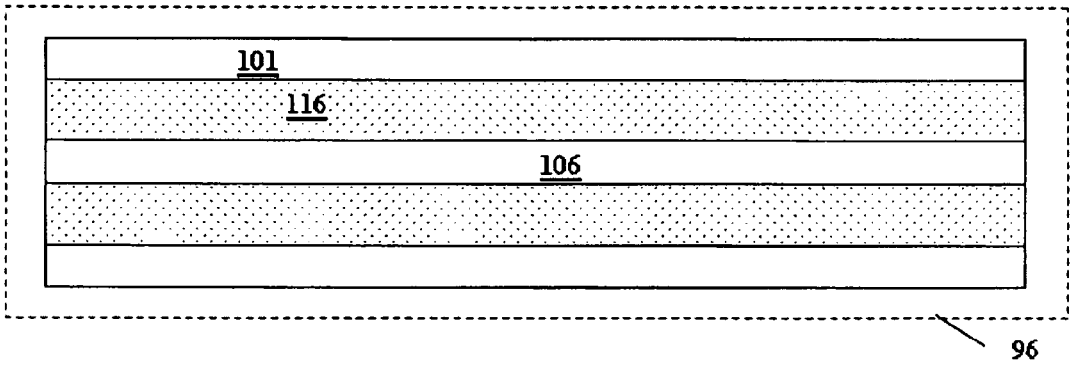
FIG. 2A is a side view of the original fiber.

There are various ways to manufacture this sensor 98. One of the easier methods includes obtaining a commercially available optical fiber 96 which includes a core 106, an outer protective jacket 101 and fiber cladding 116. To manufacture the sensor 98, the protective jacket 101 and the fiber cladding 116 are removed at specific positions chosen to sense the analyte (see FIG. 2A), the sensitive coating is prepared and applied to the exposed core 106. There are several commercially available optical fibers 96 suited for this task. Preferably such a fiber would have a large core 106 diameter, 1 to 1.5 mm, to provide the sensor 98 with a high signal output, although other diameters can produce acceptable results.

The procedure to remove the jacket, described below, assumes the use of fibers 96 which are made of a glass core 106, a plastic cladding 116, and a plastic jacket 101. This procedure also assumes that the reagent used is sensitive to chloride ions. For other reagents and chemical species the procedure may vary slightly.

Figure 3:
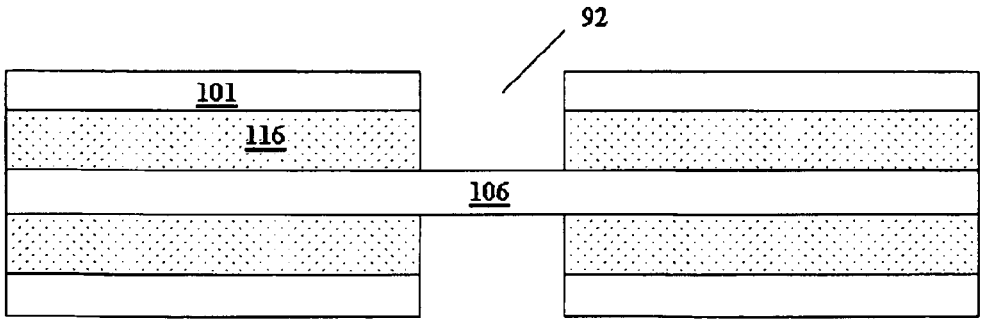
FIG. 3 is a side view of the sensing fiber, with the cladding and jacket removed.

Manufacture of the sensor 98 from an optical fiber 96 requires removal of the plastic cladding 116 and the plastic jacket 101 surrounding the core 106 at specific regions 92 where sensitivity is required. This removal can be accomplished either by chemical means, by mechanical means (using a blade), or through the use of a heat source, that burns away the jacket 101 and the plastic cladding 116. Through either method chosen, the glass core 106 is exposed to the outside environment and can be coated with the chloride ion sensitive coating. The result is the stripped region 92 of the fiber shown in FIG. 3 where the original jacket 101 and cladding 116 have been removed. Although this illustration shows a single stripped region 92, multiple sections can be stripped away from the sensor as well; or the entire length of the core 106 can be exposed.

The following describes one method for the preparation of a single type of sensitive coating; however, there are numerous types of sensitive coatings, whose preparation will likely vary. Using a fume hood, two grams of PolyVynil Acetate, PVA, is added to a beaker containing 100 ml of acetone. The resulting solution is transparent but has a viscosity higher than that of acetone. 10 mg of Lucigenin is added to the acetone/PVA solution turning the original clear solution into a yellowish color.

A few drops of the solution are applied to the surface of a microscope slide and the stripped region 92 of the fiber is placed in contact with these drops. Upon contact, a coating is formed over the surface of the glass core fiber 106. To assure uniform coating of the surface of the fiber core 106, the fiber 96 is rotated around its axis while in contact with the drops. Since acetone is a solvent that evaporates quickly, the coating must be applied very quickly to the surface of the fiber core 106 while the drops are still wet. If the procedure takes too long, the coating will harden over the slide surface and no material will be transferred to the surface of the exposed core 106.

TABLE 1

Indices of refraction and diameters of different sections of the fiber.

| | Core | Cladding | Sensitive coating |
|---|---|---|---|
| Diameter (mm) | 1.000 | 1.035 | 1.035 |
| Index of refraction | 1.457 | 1.376 | 1.47 |

Figure 4:
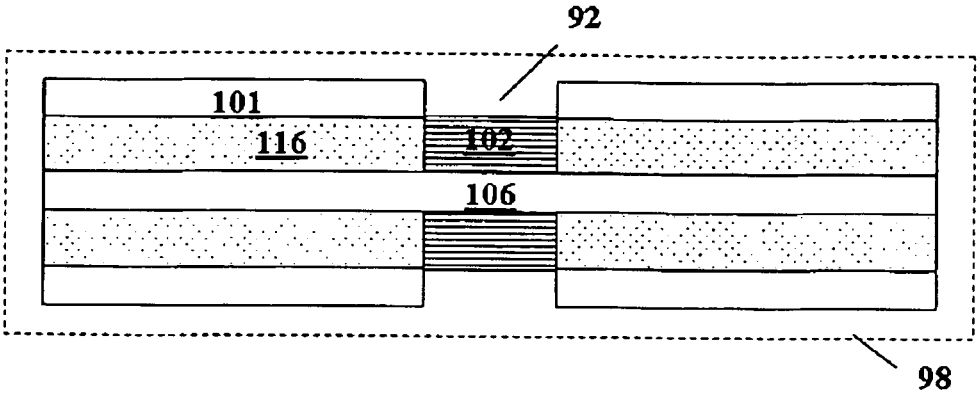
FIG. 4 is a side view of the sensing fiber of the present invention, showing the sensitive region.

FIG. 4 illustrates the resulting sensor 98 obtained from this procedure with its fiber core 106, plastic cladding 116, and its new sensitive region 102. The resulting index of refraction of this region is similar to the index of refraction of PVA, n=1.47 (see Table 1).

Although the index of refraction of the sensitive coating 102 is higher than the index of refraction of the core 106, there is still a considerable amount of fluorescent light injected into the fiber core 106. There are various reasons behind this phenomenon; such as, the fiber core 106 has a large diameter, allowing the propagation of low attenuation leaky modes. Leaky modes are light rays that are not totally internally reflected at the core/cladding boundary but still propagate for very long distances in the fiber core 106. These types of light rays are particularly useful for optical fibers that have a relatively short length, 1 m or less. Also, much of the light from the sensitive region 102 couples into the fiber core 106 as low attenuation leaky modes. Once the leaky rays enter the region of the core 106 surrounded by the plastic cladding 116, some of them couple into regular bound modes.

The same procedure discussed above can be used to prepare polycarbonate fibers. These fibers have the advantage of having a core index of refraction, 1.582, that is higher than the index of refraction of PVA, 1.47. In this case, fluorescence from the sensing section of the fiber is injected into the fiber core via evanescent wave coupling. Some leaky modes also propagate along the fiber.

Another embodiment of this type of sensor requires access to an optical fiber drawing tower facility. Using a drawing tower, it is possible to manufacture a custom made optical fiber with a high refractive index core surrounded by a fluorescent cladding. Schott Glass offers a few commercially available rod glasses, with a diameter of 32 mm, for optical fiber drawing. Once a preform is chosen, it is introduced in the drawing tower furnace and pulled into a small diameter fiber, between 1 and 1.5 mm. The resulting fiber is then coated inline with the Acetone/PVA/lucigenin solution described previously. The final result is a long length optical fiber completely coated with a chloride ion sensitive cladding.

Figure 5:
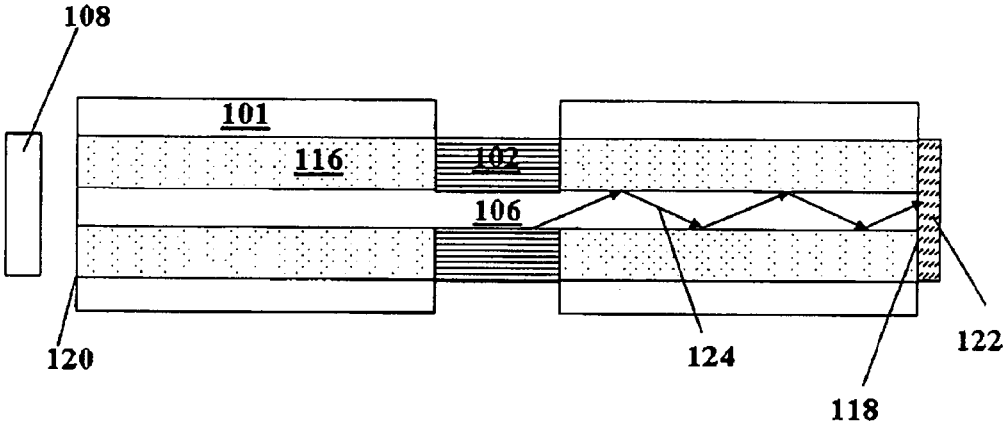
FIG. 5 is a side view of an alternate embodiment of the sensing fiber of the present invention showing a reflecting surface at the second terminus of the fiber.

Looking at FIG. 5, an additional embodiment can include a reflector 122 at the terminus of the sensor 98 opposite to the detector 108, increasing the light signal through redirecting backward propagating modes 124 towards the detector 108 increasing the fluorescent signal.

Figure 6:
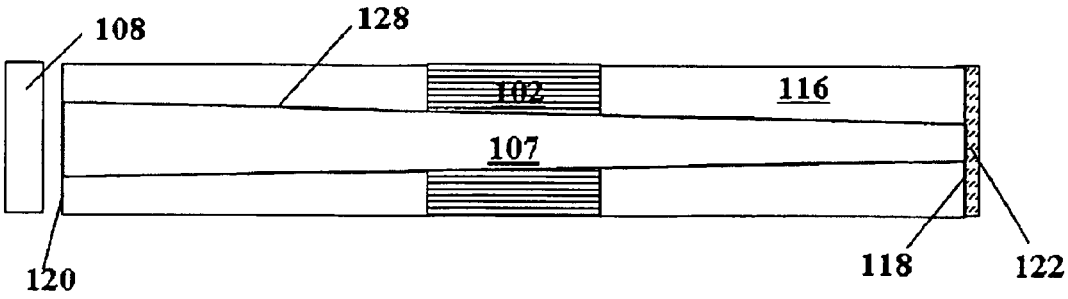
FIG. 6 is a side view of an alternate embodiment of the sensing fiber of the present invention showing a tapered core.

Yet another embodiment, shown in FIG. 6, includes the use of a sensitive optical fiber sensor 98 with a tapered core 107, generally diverging as the fluorescence 104 propagates from the sensitive region 102 of the sensor 98 to the detector 108. This tapered core 107 configuration has the advantage of coupling more light into the fiber core 107 than the other configurations increasing the signal of the sensor 98. With a tapered optical fiber core 107, light rays that otherwise would radiate away from the fiber core 107 are coupled as low loss bound modes and propagate for much longer lengths. This fiber can be manufactured using a drawing tower with a tapered glass preform. Alternatively, this fiber can also be manufactured manually by those skilled in the shaping of glass.

Figure 7:
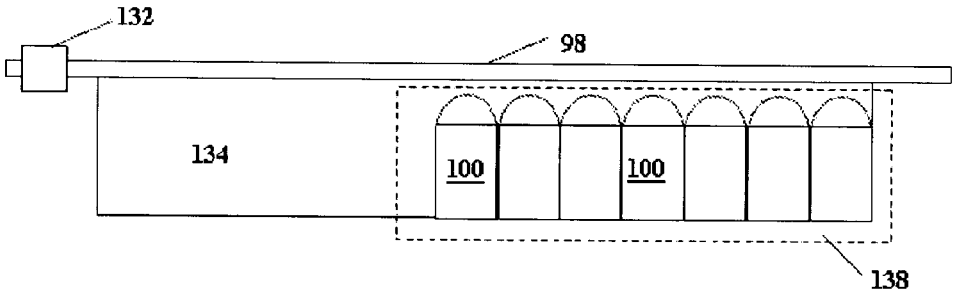
FIG. 7 is a side view of an alternate embodiment of the sensing fiber of the present invention, showing a linear array of LEDs.

In yet another embodiment, seen in FIG. 7, a plurality of light sources, such as UV LEDs, are mounted on a support 134 in a linear array along the length of the sensor 98, each light 100 simultaneously emitting an excitation light transversely across the optical fiber core 106. The length of the array 138 corresponds substantially to the length of the sensitive region 102 of the optical fiber sensor 98. This arrangement can be used to increase the overall signal of the sensor 98. An optical fiber connector 132 provides protection to the end of the fiber of the sensor 98, preventing breakage, and allows a reproducible positioning of the end of the fiber sensor 98 next to the detector 126.

For the specific case of the chloride ion sensor being described, commercially available UV LEDs 100, with a peak wavelength of 375 nm, are used. The chloride ion indicator, such as Lucigenin, absorbs at this wavelength and fluoresces in the region of 505 nm. By alternately turning on and off each LED 100, it is possible to probe a specific sensitive region 102, resulting in a truly distributed sensor 98.

Figure 8:
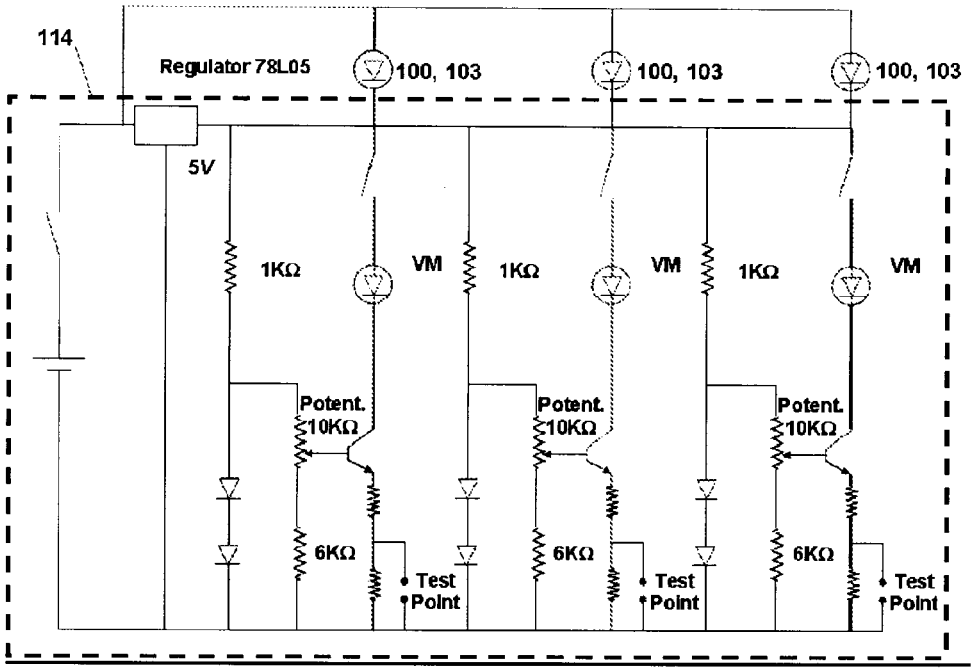
FIG. 8 is a circuit diagram enabling an alternate embodiment of the present invention.

The power supply 114 must be designed in such a way that it does not exceed the current limitations of the LEDs 100. A preferred schematic of the circuit for a portable power supply is shown in FIG. 8. Specifically, FIG. 8 describes the circuit of the power supply 114 that controls the outnut current to the illumination source 100 and 103. This specific circuit is designed to power three different sources, either simultaneously or one at a time. "VM" is the indicator LED and "Potent." 10KΩis a potentiometer. By varying the resistance of the potentiometer, it is possible to increase or decrease the current to the illumination sources which also increases or decreases the light intensity of these sources.

Another alternative embodiment of this excitation scheme is possible. This involves the replacement of the UV LEDs 100 with a strip of OLEDs (Organic Light Emitting Diodes). Although a recent technology, OLEDs could, in principle, be incorporated into a strip over which the optical fiber sensor can be mounted.

Figure 9:
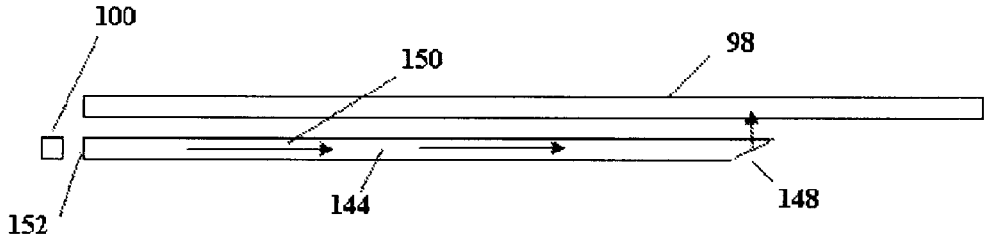
FIG. 9 is a diagram showing the operation of an excitation optical fiber with a 45 degrees distal end.

FIG. 9 shows an alternate embodiment that uses an excitation optical fiber 144 to transversely probe the sensitive optical fiber 98. In this case, the excitation fiber 144 serves as a light guide for the excitation light 150 and is deployed parallel to the sensitive optical fiber 98. The excitation fiber 144 is manufactured with a reflecting distal end face 148 at an angle of approximately 45 degrees, although other angles may also work, which redirects the excitation light 150 towards the sensitive optical fiber 98. The excitation light is generated by a UV LED 100 source at the proximal end of the fiber 152, and introduced axially. The position of the reflecting distal end face 148 can be changed to probe different sections of the sensing fiber 98; or multiple excitation fibers can be used, each probing a specific area of the sensitive optical fiber 98.

Figure 10:
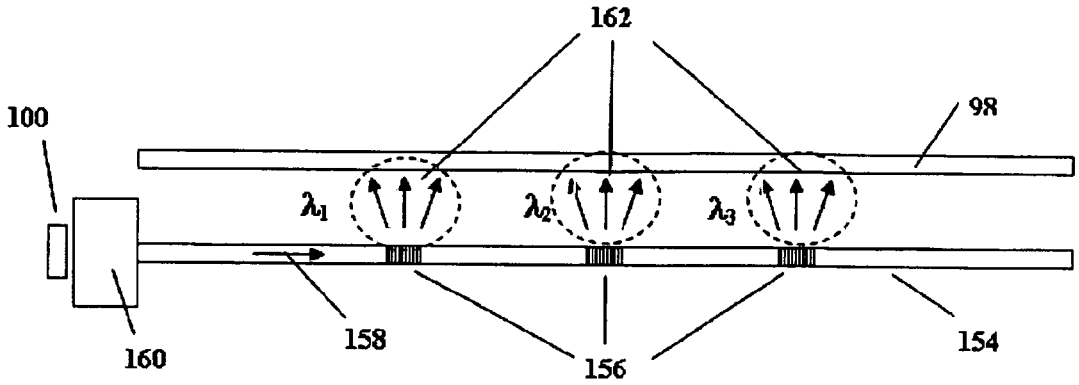
FIG. 10 is a diagram showing the operation of an excitation optical fiber made of several long period bragg gratings.

Yet another alternate embodiment, seen in FIG. 10, uses an excitation optical fiber 154 having several long period Bragg gratings 156. This excitation fiber 154 is also deployed along the sensitive optical fiber 98 and illuminates several of its sections through the long period gratings 156. Each grating 156 is designed to couple light from a bound mode core 158 of the excitation optical fiber 154 into radiation modes 160 at specific wavelengths, $\lambda_i$, within the absorption spectrum of the fluorescent dye. In this case, the light from a broadband UV LED 100 excitation light source passes through a monochromator 160 that scans the wavelengths within the absorption spectrum of the dye. When the monochromator 160 is tuned to a wavelength $\lambda_1$, only the grating 156 tuned to this wavelength couples the light towards the sensitive optical fiber 98 and the illuminated section corresponds to the position of this specific Bragg grating 156. The procedure can be repeated for other wavelengths.

Figure 11:
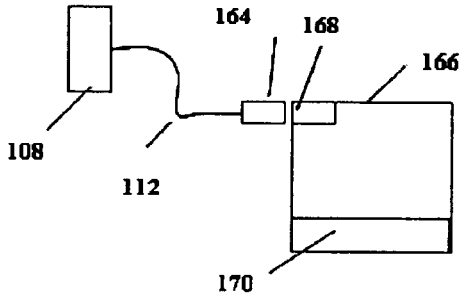
FIG. 11 is a block diagram of the detection system of the present invention.
Figure 12:
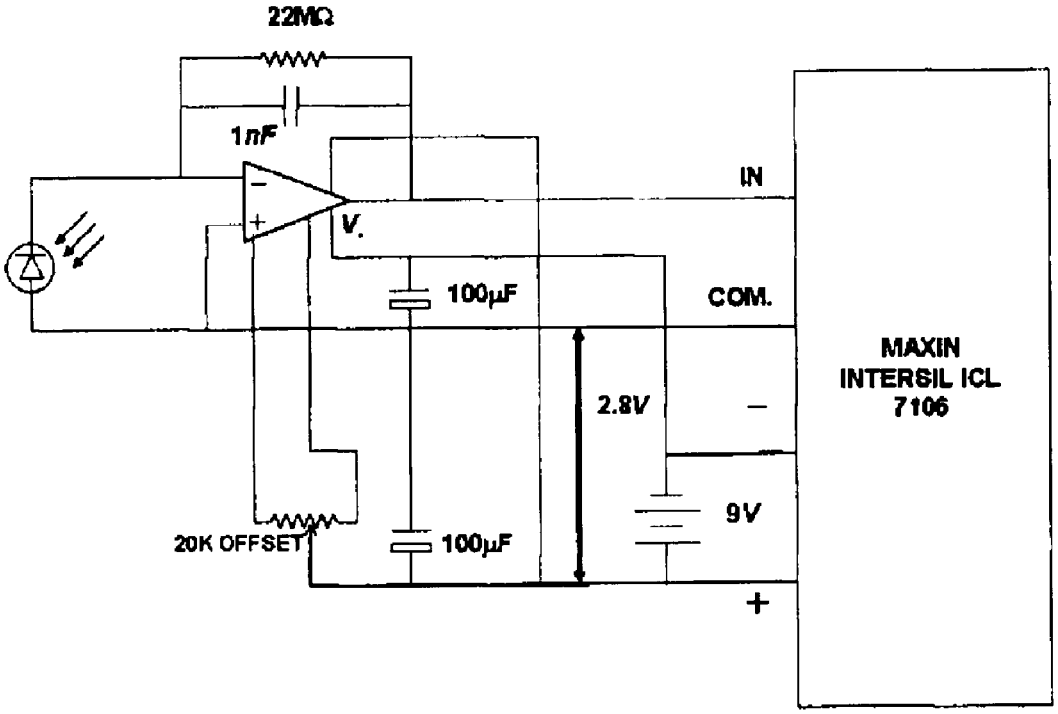
FIG. 12 is a circuit diagram enabling an alternate embodiment of the present invention.

An embodiment of the detection system is shown in FIG. 11. It consists of a silicon photodetector 108, a photodetector cable 112, a male connector 164 and a read out unit 166. The male connector 164 is connected to a female connector 168 in the read out unit 166. The photodetector 108 is mounted inside a light tight enclosure (not shown) which can be connected to the optical fiber connector. The leads of the detector are connected to a cable that transmits the photo-electric signal to an amplification circuit (shown in FIG. 12). The circuit amplifies the signal and its intensity is displayed in the display 170 of the read out unit 166.

Figure 13:
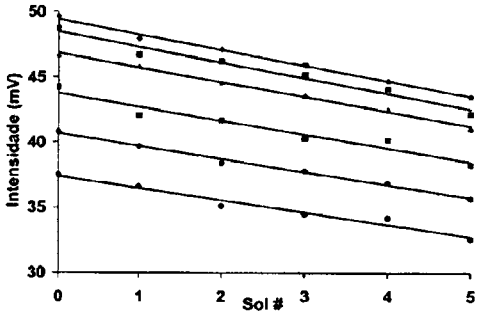
FIG. 13 is a graph of data gathered with the present invention.

The present invention described above was built and tested in different concentrations of salt water. Data for this experiment is illustrated in FIG. 13. As the salt concentration increases, the optical fiber signal decreases. Notice that the read out response is linear with salt concentration in water. Each curve corresponds to detector response whenever the fiber end tip was at different distances from the detector. Accordingly, the upper curve corresponds to the fiber end face closest to the detector (Δx=0 mm), whereas the lowest curve corresponds to a distance of 2 mm from the detector.

TABLE 2

Numerical data of FIG. 16. Six different solutions of salt water were used. The fiber end face was positioned at six different distances, Δx, from the detector.

| Solution # | Salt concentration (g/ml) | Signal (mV) Δx = 0 mm | Δx = 0.3 mm | Δx = 0.6 mm | Δx = 1.0 mm | Δx = 1.5 mm | Δx = 2.0 mm |
|---|---|---|---|---|---|---|---|
| 0 | 0 | 49.6 | 48.7 | 46.7 | 44.2 | 40.8 | 37.5 |
| 1 | 7 | 47.9 | 46.7 | 45.8 | 42.1 | 39.7 | 36.6 |
| 2 | 14 | 47.1 | 46.2 | 44.6 | 41.7 | 38.4 | 35.1 |
| 3 | 21 | 46.0 | 45.2 | 43.6 | 40.3 | 37.8 | 34.5 |
| 4 | 28 | 44.7 | 44.1 | 42.5 | 40.2 | 36.9 | 34.2 |
| 5 | 35 | 43.5 | 42.2 | 41.1 | 38.3 | 35.7 | 32.6 |

The slopes of these curves are similar demonstrating that the sensor sensitivity is reproducible. This data also shows signal reversibility provided the different distances of the fiber end face to the detector is accounted for. Signal reproducibility was also observed whenever the fiber end face was disconnected from the detector and connected back. The concentration of each solution as well as the actual data for the graph of FIG. 13 is shown in Table 2. This experiment demonstrated that the sensor has a linear response, is robust and its signal is stable, reversible and reproducible.

The present invention, in its various forms, can be used in many different applications, including but not limited to, monitoring chloride ion intrusion in concrete structures (the cause of rebar corrosion and subsequent structural failure), monitoring chloride ions in aircraft structures (the cause of pit corrosion), measuring the contents of chloride and other ions in the soil of plants, and measuring the concentration of chloride ions in desalinators. When properly modified, it can also be used to detect other types of ions, molecules and temperature provided a proper indicator and polymeric matrix can be chosen.

Figure 14:
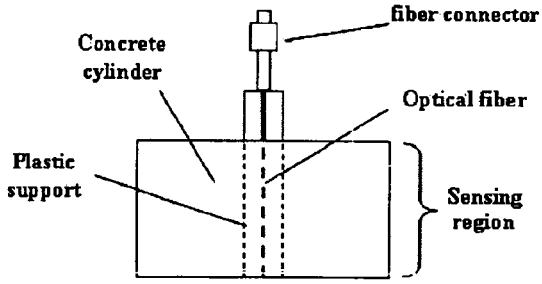
FIG. 14 is a plan view of the present invention installed in situ within a structure.
Figure 15:
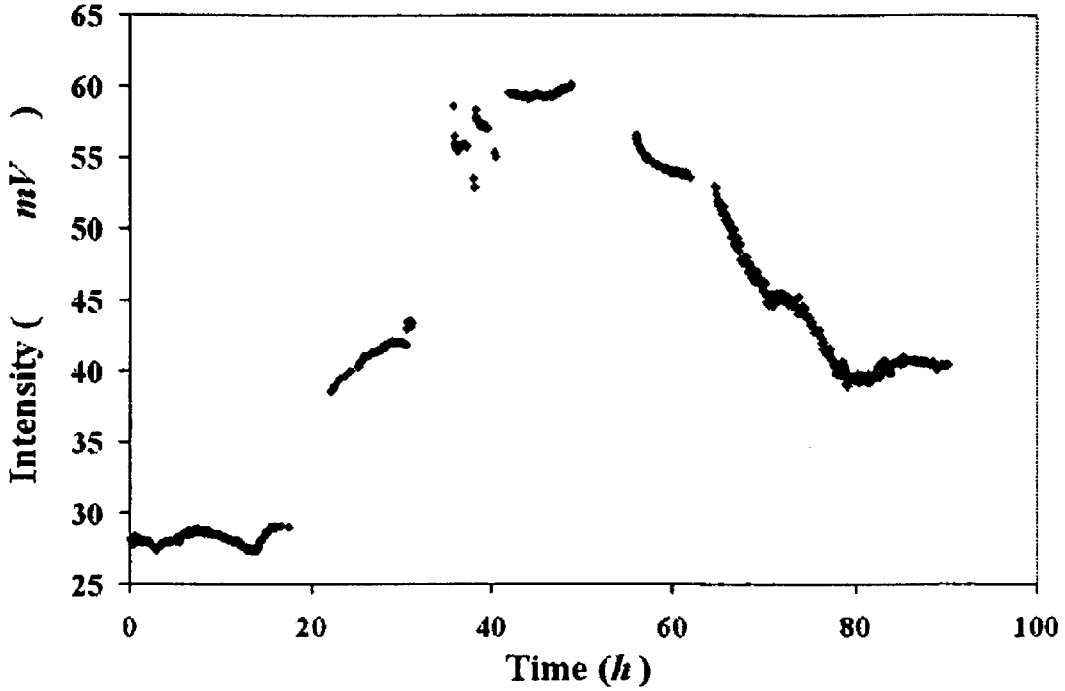
FIG. 15 is a graph of data gathered from the present invention.

Due to the sensor modular design, it is possible to embed the sensor sub-system in a concrete structure while exposing the fiber end tip and its input power port to the outside environment (see FIG. 14). Accordingly, a test of the sensor was made to determine its response while embedded inside a cylindrical concrete. The concrete specimen was then subjected to salt water (pounded) and the sensor signal was monitored for several days. The sensor response during the last 90 hours of this experiment is shown in FIG. 15. The following is a timeline of events of the experiment where T=0 h corresponds to day 20:

1. The concrete sample was cast with the fiber sensor two weeks prior to day 1.
2. On day 1, at T=−460 h, the top of the cylindrical concrete was subjected 100 ml of salt water at the saturation point.
3. On day 19 the salt water was replaced with pure water (T=−28 h).
4. T=0 h in FIG. 15 corresponds to day 20 (T=0 h). The signal level of the fiber is below 30 mV indicating a high concentration of chloride due to the previous exposure to salt water.
5. At T=+20 h the signal of the detector starts to increase because of the decrease of the concentration of chloride ions due to permeation of pure water that started on day 19 (48 h ago).
6. At T=+40 h the signal of the sensor reaches its maximum level, around 60 mV.
7. On day 22 pure water was replaced with salt water again (T=+48.9 h).
8. Between T=+50 h and T=+60 h the signal from the sensor starts to decrease due to the increasing concentration of chloride ions around the monitoring point.
9. At T=+80 h the signal reaches is lowest level and becomes stable.

The experiment was terminated around T=+90 h.

While the present invention has been described with regards to particular embodiments, it is recognized that additional variations of the present invention may be devised without departing from the inventive concept. Many improvements, modifications, and additions will be apparent to the skilled artisan without departing from the spirit and scope of the present invention as described herein and defined in the following claims.

What is claimed is:

1. A sensing system, comprising:

a sensitive optical fiber having a core with a cladding having at least one sensitive region being sensitive to at least one measurand and being configured for a spatial resolution of 5 mm or less, said sensitive optical fiber being optically affected in a monotonic relationship by the presence of said measurand found in an environment surrounding said sensitive optical fiber;

at least one probing light source producing a probing light and being directed from the exterior of said cladding into said sensitive region thereof for illuminating each sensitive region individually, one at a time, said probing light interacts individually with each said sensitive region such that a modified probing light is generated therefrom, each such modification having been substantially caused by the presence of said measurand and said modified probing light being substantially coupled into said core as a light signal with high signal intensity associated with each said sensitive region;

a detector means in axial optical communication with a first terminus of said sensitive optical fiber, being configured to receive said light signal upon exiting said first terminus, to measure an intensity of said light signal over a given range of wavelengths and to correlate said intensity with an electric signal;

a signal processing means being in data communication with said detector means, said electric signal being transmitted to said signal processing means;

a display means being in data communication with said signal processing means, said electric signal is correlated to a quantity of said measurand being measured, said quantity being transmitted and displayed on said display means; and a power supply configured to provide power to said probing light source, said signal processing means, and said display means.

2. The sensing system of claim 1 wherein said core has a tapered geometry, generally diverging towards said detector means as said light signal propagates from said sensitive region of said sensitive optical fiber to said detector, said tapered geometry being adapted to minimize loss of intensity of said light signal.

3. The sensing system of claim 1 wherein said core is doped with a fluorescent substance forming a fluorescent core, said fluorescent core increasing the intensity of said light signal being delivered to said detector means.

4. The sensing system of claim 1, wherein the refractive index of said core is smaller than or equal to the refractive index of said sensitive region for enabling a coupling from said sensitive region to said core.

5. The sensing system of claim 1 wherein said sensitive region is manufactured with a reagent selected from the group consisting of a colorimetric reagent, an absorption based reagent and a fluorescent reagent.

6. The sensing system of claim 1 wherein said measurand is selected from the group consisting of the strain the optical fiber is subjected to, the concentration of a chemical species surrounding said sensitive region of the optical fiber, the temperature of the environment surrounding said sensitive region of the optical fiber and the pressure of the environment surrounding said sensitive region of the optical fiber.

7. The sensing system of claim 1 wherein said probing light source is selected from the group consisting of an ultraviolet light emitting diode, a broad band visible light emitting diode and an organic light emitting diode.

8. The sensing system of claim 1 wherein said probing light source has a maximum size of 5 mm and said probing light source is capable of producing a spatial resolution of at least 5 mm.

9. The sensing system of claim 1 wherein said probing light source has a minimum size of 5 mm and said probing light source is capable of producing a spatial resolution of at most 5 mm.

10. The sensing system of claim 1 wherein said at least one probing light source is a plurality of probing light sources positioned in a linear array along said sensitive region of said sensitive optical fiber whereby said sensing system is a distributed optical fiber sensor.

11. The sensing system of claim 10 wherein said plurality of probing light sources behave as a single light source by emitting said probing light simultaneously at an angle, towards said sensitive region providing an enhanced light signal.

12. The sensing system of claim 10 wherein said plurality of probing light sources emits said probing light consecutively, one by one, at an angle, towards said sensitive region.

13. The sensing system of claim 10 wherein said plurality of probing light sources emits said probing light in adjacent groups, simultaneously, at an angle towards said sensitive region, one group at a time, providing an enhanced light signal.

14. The sensing system of claim 10 wherein each of said plurality of probing light sources are configured each to independently emit said probing light at an angle towards said sensitive region one by one, each of said plurality of probing light sources independently illuminating a discrete portion of said sensitive region.

15. The sensing system of claim 10 wherein said plurality of probing light sources emits said probing light in non-adjacent groups, simultaneously, at an angle, towards said sensitive region, one group at a time.

16. The sensing system of claim 1 wherein said detector means is a silicon photo detector positioned at the first terminus end of the sensitive optical fiber.

17. The sensing system of claim 1 wherein a reflector is positioned at a second terminus of said sensitive optical fiber, wherein said reflector increases said light signal through redirecting backward propagating modes towards said detector means.

18. The sensing system of claim 1, wherein said probing light source is transmitted by an illumination optical fiber, said illumination fiber having a plurality of long period Bragg gratings, said illumination fiber being positioned parallel to said sensitive optical fiber, said long period Bragg gratings illuminating at an angle said sensitive region of said sensitive optical fiber at discrete positions, wherein a probing light source introduces a probing light into a monochromator, said monochromator filtering the probing light to a specified wavelength, said probing light at a specified wavelength being axially introduced to said illumination optical fiber, said probing light at a specified wavelength propagating to its specified long period grating having similar wavelength characteristics, and said specified long period Bragg grating redirecting the probing light at an angle towards said sensitive region of said sensitive fiber, wherein each grating is designed to couple light from a bound mode core of said illumination optical fiber into radiation modes at specific wavelengths, and wherein the radiation modes of a specific wavelength illuminate the sensitive cladding region.

19. The sensing system of claim 18, wherein said monochromator can be incrementally tuned to filter the probing light to a specific wavelength, said specific wavelength corresponding to a specific long period Bragg grating and said long period Bragg grating being located at a known point along said illumination optical fiber.

20. The sensing system of claim 1 wherein said sensitive optical fiber and said probing light source are mounted to a support to permit installation in situ within a body and wherein at least one measurand is being detected within the body at *at* least one point that is being probed.

21. The sensing system of claim 1 wherein said probing light source comprises at least one white light broadband source that interacts with said sensitive region of said sensitive optical fiber cladding, such that a portion of said broadband light is absorbed by said sensitive region to form a partially absorbed broadband light, said absorption having been substantially affected by the presence of said measurand, and said partially absorbed broadband light being substantially coupled into said core as a light signal in the form of a plurality of bound modes and leaky rays.

22. The sensing system of claim 1, wherein said probing light source comprises at least one ultraviolet LED excitation light source, said excitation light source producing a probing light, and said excitation light source being adjacent to said sensitive optical fiber at said sensitive region of said cladding;

wherein said detector means comprises a silicon photo-detector; wherein said probing light interacts with said sensitive region of said sensitive optical fiber, such that a portion of said probing light is absorbed by said sensitive region, said sensitive region emits a fluorescent light upon excitation by the probing light, said fluorescent light is substantially affected by the presence of said measurand, said fluorescent light is substantially coupled into said core as a light signal, and said light signal is transmitted to said first terminus of said sensitive fiber; wherein said silicon photo-detector receives said light signal upon exiting said first terminus of said sensitive optical fiber, said silicon photo-detector monotonically correlates the intensity of said light signal over a given range of wavelengths with an electric signal, said electric signal is transmitted to said signal processing means; and wherein said electric signal is correlated to a measurand in said signal processing means, and said measurand is transmitted and displayed on said display means.

23. The sensing system of claim 1, in which said fiber is coated with different sensitive reagents, for enabling each said sensitive coating to be sensitive to a particular chemical species, in which each said coating has a specific length that defines the spatial resolution of the sensing fiber.

24. The sensing system of claim 1, further including a plurality of LEDs for controlling the signal intensity and sensitivity of the sensitive regions.

25. The sensing system of claim 24 in which a varying current is input to said LEDs for controlling the signal intensity and sensitivity of the sensitive regions.

26. The sensing system of claim 25 further including a read out for reading the integrated light intensity of the sensitive regions for making measurements.

27. The sensing system of claim 1 wherein said probing light source illuminates the sensitive region of the sensitive optical fiber producing an illumination length such that the spatial resolution of the sensor is equal to said illumination length whenever the length of said sensitive region is greater than said illumination length and to the length of said sensitive region whenever the length of said sensitive region is less than said illumination length and the illumination length does not simultaneously illuminate multiple separate sensitive regions.

28. The sensing system of claim 1 wherein said probing light source is repositionable to illuminate different discrete regions along the length of the fiber.

29. A sensing system, comprising:

a sensitive optical fiber having a core with a cladding having at least one sensitive region being sensitive to at least one measurand;

at least one probing light source producing a probing light and being directed from the exterior of said cladding into said sensitive region thereof for illuminating each sensitive region individually, one at a time;

a detector means in axial optical communication with a first terminus of said sensitive optical fiber;

a signal processing means being in data communication with said detector means;

a display means being in data communication with said signal processing means; and a power supply configured to provide power to said probing light source, said detector means, said signal processing means, and said display means, wherein said probing light is transmitted by an illumination optical fiber, said illumination optical fiber having an angled reflecting distal end face, said illumination optical fiber being positioned parallel to said sensitive optical fiber, said angled reflecting distal end face being configured to illuminate said sensitive region, at an angle, with said probing light, wherein a probing light source axially introduces said probing light into said illumination optical fiber, said probing light being coupled into the core of said illumination optical fiber, said probing light being transmitted along the length of said illumination optical fiber towards said angled reflecting distal end face, and said probing light being reflected at an angle towards said sensitive region by said angled reflecting distal end face to cause said probing light to interact with said sensitive region.

30. The sensing system of claim 29, wherein said angled reflecting distal end face is repositionable to illuminate a discrete region of said sensitive optical fiber.

31. The sensing system of claim 29, wherein a plurality of said illumination fibers, each having an angled reflecting distal end face, is positioned parallel to said sensitive optical fiber, said angled reflecting distal end faces of each said illumination fiber being positioned at discrete regions along said sensitive optical fiber.

*32. A sensing system, comprising:*

*an optical fiber having a core surrounded by a cladding without a barrier coating having at least one sensitive region and being sensitive to at least one measurand, said core not having the sensitivity of said at least one sensitive region;*

*at least one probing light source for producing a probing light being directed at an angle towards said at least one sensitive region thereof for illuminating said at least one sensitive region,*

*when said at least one probing light source interacts individually with said at least one sensitive region, a modified probing light is generated therefrom, said modification of said at least one probing light having been substantially caused by the presence of said measurand; and*

*said at least one modified probing light being substantially coupled into said core as a light signal.*

*33. The sensing system of claim 32 further comprising a detector in axial optical communication with a first terminus of said optical fiber, being configured to receive said light signal upon exiting said first terminus, to measure the intensity of said light signal over a given range of wavelengths and to correlate said intensity with an electric signal.*

*34. The sensing system of claim 33 further comprising a signal processor in data communication with said detector; wherein the electric signal is correlated to a quantity of the measurand being measured.*

*35. The sensing system of claim 34 further comprising a display in data communication with said signal processor and a power supply configured to provide power to said probing light source, said signal processor, and a display.*

*36. The sensing system of claim 34 further comprising a display in data communication with said signal processor and a power supply configured to provide power to said at least one probing light source, said detector, said signal processor, and a display.*

*37. The sensing system of claim 32 wherein said at least one sensitive region comprises a reagent selected from the group consisting of a colorimetric reagent, an absorption based reagent and a fluorescent reagent.*

*38. The sensing system of claim 32 wherein said core is comprised of glass or plastic.*

*39. The sensing system of claim 32 wherein said core has a tapered geometry.*

* * * * *